(12) United States Patent
Lagrange et al.

(10) Patent No.: US 7,374,581 B2
(45) Date of Patent: May 20, 2008

(54) DYE COMPOSITION CONTAINING A PARTICULAR CATIONIC HYDRAZONE DIRECT DYE, DYEING PROCESS, USE AND MULTI-COMPARTMENT DEVICES

(75) Inventors: Alain Lagrange, Coupvray (FR); Leïla Hercouet, Neuilly Plaisance (FR)

(73) Assignee: L'Oreal, S.A., Paris (FR)

( * ) Notice: Subject to any disclaimer, the term of this patent is extended or adjusted under 35 U.S.C. 154(b) by 212 days.

(21) Appl. No.: 11/414,558

(22) Filed: May 1, 2006

(65) Prior Publication Data
US 2006/0272104 A1 Dec. 7, 2006

Related U.S. Application Data

(60) Provisional application No. 60/698,946, filed on Jul. 14, 2005.

(30) Foreign Application Priority Data
Apr. 29, 2005 (FR) .................................. 05 51128

(51) Int. Cl.
*A61K 7/13* (2006.01)
(52) U.S. Cl. .................... 8/405; 8/406; 8/407; 8/411; 8/435; 8/454; 8/552; 8/568; 546/332
(58) Field of Classification Search ............ 8/406, 8/405, 407, 411, 435, 454, 552, 568; 546/332
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 2,798,053 A | 7/1957 | Brown | |
| 2,923,692 A | 2/1960 | Ackerman et al. | |
| 3,158,608 A | 11/1964 | Raue | |
| 3,238,198 A | 3/1966 | Raue | |
| 3,915,921 A | 10/1975 | Schlatzer, Jr. | |
| 4,003,699 A | 1/1977 | Rose et al. | |
| RE30,199 E | 1/1980 | Rose et al. | |
| 4,237,243 A | 12/1980 | Quack et al. | |
| 4,509,949 A | 4/1985 | Huang et al. | |
| 4,760,132 A * | 7/1988 | Dorsch et al. ............. | 534/574 |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 6,099,592 A | 8/2000 | Vidal et al. | |
| 6,099,593 A | 8/2000 | Terranova et al. | |
| 6,284,003 B1 | 9/2001 | Rose et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 216 479 B1 | 2/1991 |
| EP | 0 714 954 B1 | 6/1996 |
| EP | 0 770 375 B1 | 5/1997 |
| EP | 1 142 559 B1 | 10/2001 |
| EP | 1 153 599 A2 | 11/2001 |
| EP | 1 155 679 A2 | 11/2001 |
| EP | 1 166 757 B1 | 1/2002 |
| ES | 409 947 A1 | 4/1976 |
| FR | 2 416 723 A1 | 9/1979 |
| FR | 2 586 913 A1 | 3/1987 |
| FR | 2 733 749 A1 | 11/1996 |
| FR | 2 750 048 A1 | 12/1997 |
| GB | 1026978 | 4/1966 |
| GB | 1153196 | 5/1969 |
| GB | 1410938 | 10/1975 |
| JP | 2-19576 A | 1/1990 |
| JP | 05-163124 A | 6/1993 |
| WO | WO 94/08969 A1 | 4/1994 |

(Continued)

OTHER PUBLICATIONS

STIC Search Report dated Dec. 17, 2007.*

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The invention relates to a dye composition for dyeing human keratin fibres and more particularly the hair, comprising a particular direct cationic hydrazone dye of formula (I)

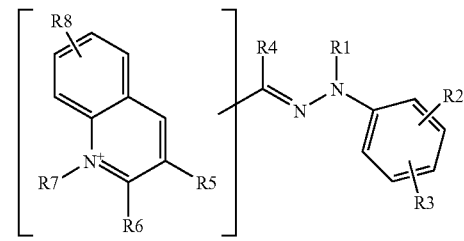

and also to processes for dyeing human keratin fibres using such a composition.

21 Claims, No Drawings

FOREIGN PATENT DOCUMENTS

| | | |
|---|---|---|
| WO | WO 94/08970 A1 | 4/1994 |
| WO | WO 95/01772 A1 | 1/1995 |
| WO | WO 95/15144 A1 | 6/1995 |
| WO | WO 96/15765 A1 | 5/1996 |
| WO | WO 01/66646 A1 | 9/2001 |

OTHER PUBLICATIONS

"Encyclopedia of Chemical Technology," Kirk-Othmer, 3rd Ed., 1982, vol. 3, pp. 896-900.

"Encyclopedia of Chemical Technology," Kirk-Othmer, 3rd Ed., 1982, vol. 15, pp. 439-458.

"Polymers in Nature" by E.A.MacGregor and C.T.Greenwood, Wiley & Sons, Ch.6, pp. 240-328, 1980.

"Handbooks of Surfactants" M.R.Porter, 1991, Blackie & Son, pp. 116-178.

French search report from FR 0551128 (foreign priority document to U.S. Appl. No. 11/414,558), dated Jan. 18, 2006, Ex. Lindner.

English language Derwent abstract of non-English language document EP 0 770 375, (1997).

English language abstract of non-English language document JP 63-169571, (1990).

English language abstract of non-English language document JP 05-163124, (1993).

* cited by examiner

DYE COMPOSITION CONTAINING A PARTICULAR CATIONIC HYDRAZONE DIRECT DYE, DYEING PROCESS, USE AND MULTI-COMPARTMENT DEVICES

FIELD OF THE INVENTION

The invention relates to the use for dyeing human keratin fibres, and more particularly the hair, of a dye composition comprising a particular direct cationic hydrazone dye, and also to processes for dyeing human keratin fibres using such a composition.

BACKGROUND OF THE INVENTION

It is known practice to dye human keratin fibres, and in particular the hair, with dye compositions containing oxidation dye precursors, which are generally known as oxidation bases. These oxidation bases are colourless or weakly coloured compounds, which, when combined with oxidizing products, give rise to coloured compounds by a process of oxidative condensation.

It is also known that the shades obtained with these oxidation bases may be varied by combining them with couplers or coloration modifiers. The variety of molecules used as oxidation bases and couplers allows a wide range of colours to be obtained.

This oxidation dyeing process consists in applying to keratin fibres oxidation bases or a mixture of oxidation bases and of couplers with an oxidizing agent, for example aqueous hydrogen peroxide solution, leaving the agents on the fibres and then rinsing the fibres. The colorations resulting therefrom are permanent, strong and resistant to external agents, especially light, bad weather, washing, perspiration and rubbing. This process, which is generally applied at basic pH, makes it possible simultaneously to dye and lighten the fibre, which is reflected in practice by the possibility of obtaining a final coloration that is lighter than the original colour. In addition, lightening of the fibre has the advantageous effect of generating a unified colour in the case of grey hair, and of bringing out the colour, i.e. making it more visible, in the case of naturally pigmented hair.

It is also known practice to dye human keratin fibres with a direct dye. The process conventionally used in direct dyeing consists in applying to the keratin fibres direct dyes, which are coloured and colouring molecules that have affinity for the fibres, leaving the dyes on the fibres and then rinsing the fibres.

It is known practice, for example, to use nitrobenzene, anthraquinone, nitropyridine, azo, xanthene, acridine, azine or triarylmethane direct dyes.

The colorations resulting therefrom are colorations that are temporary or semi-permanent since the nature of the interactions linking the direct dyes to the keratin fibre, and their desorption from the surface and/or core of the fibre are responsible for their poor dyeing power and their poor fastness with respect to washing or perspiration. These direct dyes are also generally light-sensitive due to the poor resistance of the chromophore with respect to photochemical attack, and lead over time to fading of the coloration of the hair. In addition, their light-sensitivity is dependent on their uniform distribution or their distribution as aggregates in the keratin fibre.

It is known practice to use direct dyes in combination with oxidizing agents. However, the direct dyes are generally sensitive to the action of oxidizing agents such as aqueous hydrogen peroxide solution, and reducing agents such as sodium bisulfite, which makes them generally difficult to use in lightening direct dyeing compositions based on aqueous hydrogen peroxide solution and based on a basifying agent, or in oxidation dye compositions in combination with precursors such as oxidation bases or couplers.

Moreover, it is known practice to use, for the dyeing of keratin fibres, dyes containing a hydrazone unit, in particular in documents EP 1 166 757, EP 1 142 559, EP 1 153 599 and EP 1 155 679. In these documents, the dyes are of a different type from those that are useful in the present invention. Document U.S. Pat. No. 3,238,198 also discloses hydrazone dyes of the same type as those that are useful in the present invention. However, these compounds are not described for dyeing human keratin fibres.

There is a real need to find chromatic direct dyes that allow human keratin fibres to be dyed, under mild conditions, as strongly as oxidation dyes, which are just as light-fast as the latter dyes, and which are also resistant to bad weather, washing and perspiration, and also sufficiently stable in the presence of oxidizing and reducing agents to be able simultaneously to obtain lightening of the fibre or to be combined with oxidation dyes.

In addition, there is a need to provide dyes that show good harmlessness and that show less selectivity compared with standard dyes.

DETAILED DESCRIPTION OF THE INVENTION.

These aims are achieved with the present invention, one subject of which is the use for dyeing human keratin fibres, and more particularly the hair, of a composition comprising, in a suitable medium, at least one direct cationic hydrazone dye of formula (I) below, or a tautomeric form thereof:

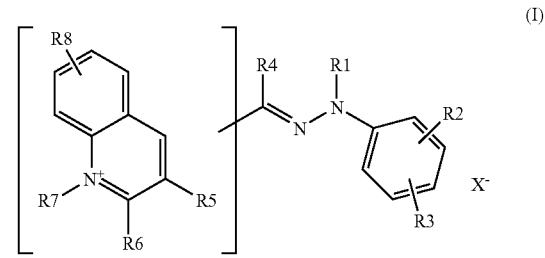

in which
- $R_1$ and $R_7$ denote, independently of each other, a $C_1$-$C_6$ alkyl, $C_1$-$C_6$ hydroxyalkyl, benzyl, p-chloro-benzyl or phenyl radical,
- $R_4$ denotes a hydrogen atom or a $C_1$-$C_6$ alkyl radical,
- $R_2$, $R_3$, $R_5$, $R_6$ and $R_8$ denote, independently of each other, a hydrogen atom, a $C_1$-$C_6$ alkyl radical, a halogen atom, a nitro radical, a $C_1$-$C_6$ alkoxy radical, an amino radical, a $C_1$-$C_6$ alkylamino radical, a $C_1$-$C_6$ dialkylamino radical, a sulfamoyl radical, a $C_1$-$C_6$ dialkylsulfamoyl radical, a $C_1$-$C_6$ dihydroxy-alkylamino radical or a $C_1$-$C_6$ dihydroxy-alkylamino radical,
- $R_1$ may form with $R_2$ or $R_3$ and the adjacent atoms a saturated or unsaturated, 5-, 6- or 7-membered ring optionally substituted with one or more $C_1$-$C_6$ alkyl radicals, or optionally fused with a benzene nucleus,
- $R_1$ and $R_4$ may form a 5-, 6- or 7-membered unsaturated ring, $R_5$ and $R_6$ may form, with the adjacent atoms, a saturated or unsaturated 5-, 6- or 7-membered ring, the bonding between the hydrazone group and the quinoline group possibly taking place on each of the carbon atoms of the quinoline heterocycle, and also in place of the groups $R_5$, $R_6$ and R, X⁻ denotes an anion that ensures the neutrality of the molecule, such as an anion derived from a mineral or organic acid, for instance hydrochloric acid, sulfuric acid, tartaric acid, lactic acid or methanesulfonic acid, the nature of the counterion not being critical.

Alkyl radicals that are intended include linear or branched methyl, ethyl, propyl, butyl, pentyl and hexyl radicals.

The compounds of the invention may be obtained from an aldehyde or a ketone and from a hydrazine derivative in two steps: condensation followed by quaternization, for example according to the scheme below:

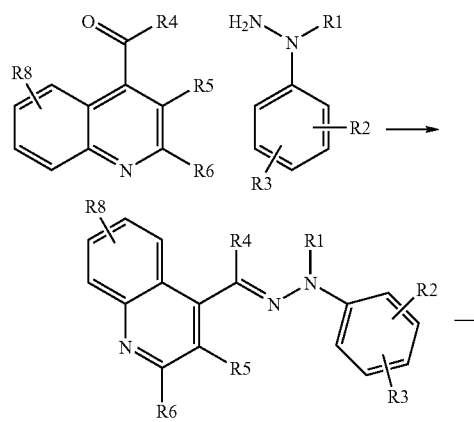

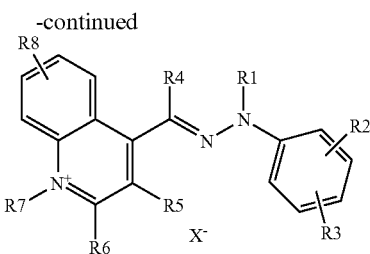

The compounds of the invention may also be obtained from an activated methylene and from a diazonium salt derivative in one step, for example according to the scheme below:

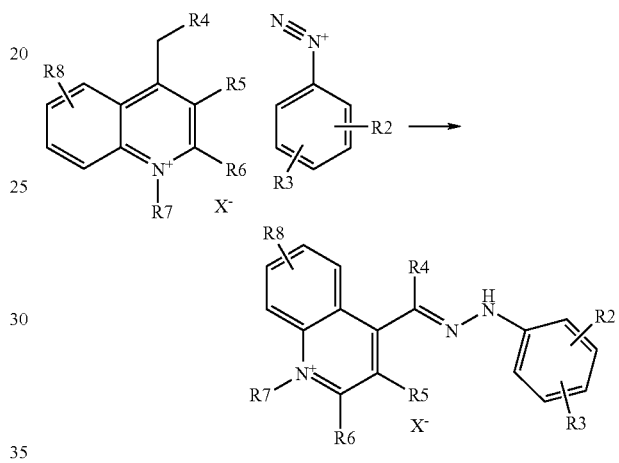

Such compounds are known in the art. Among these, mention may be made of the following compounds described in patent U.S. Pat. No. 3,158,608:

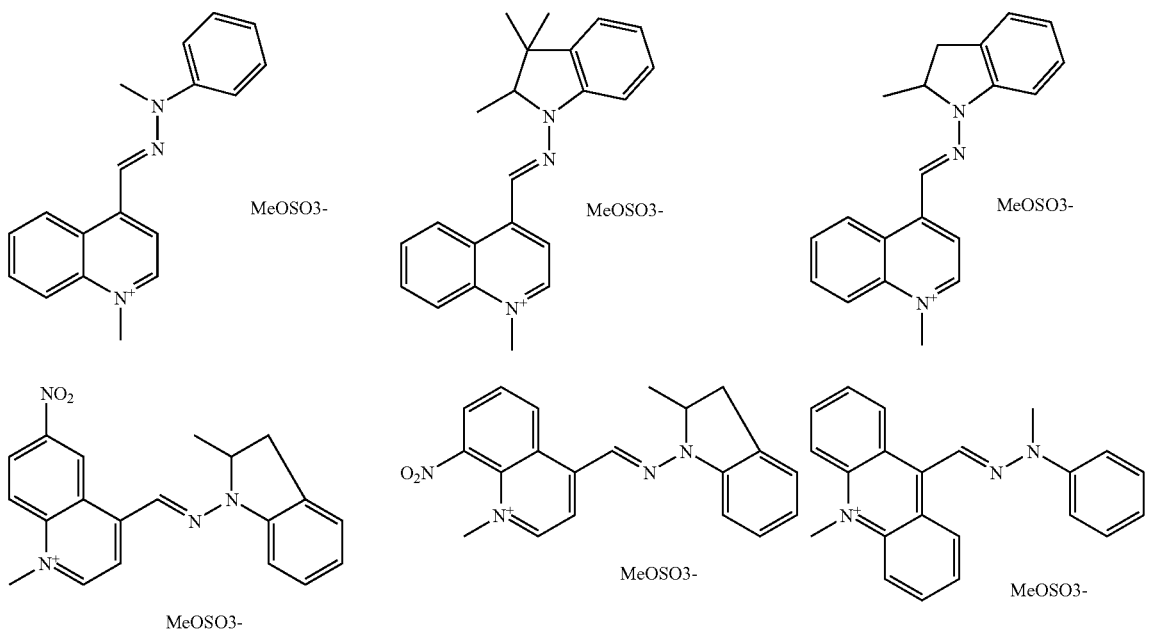

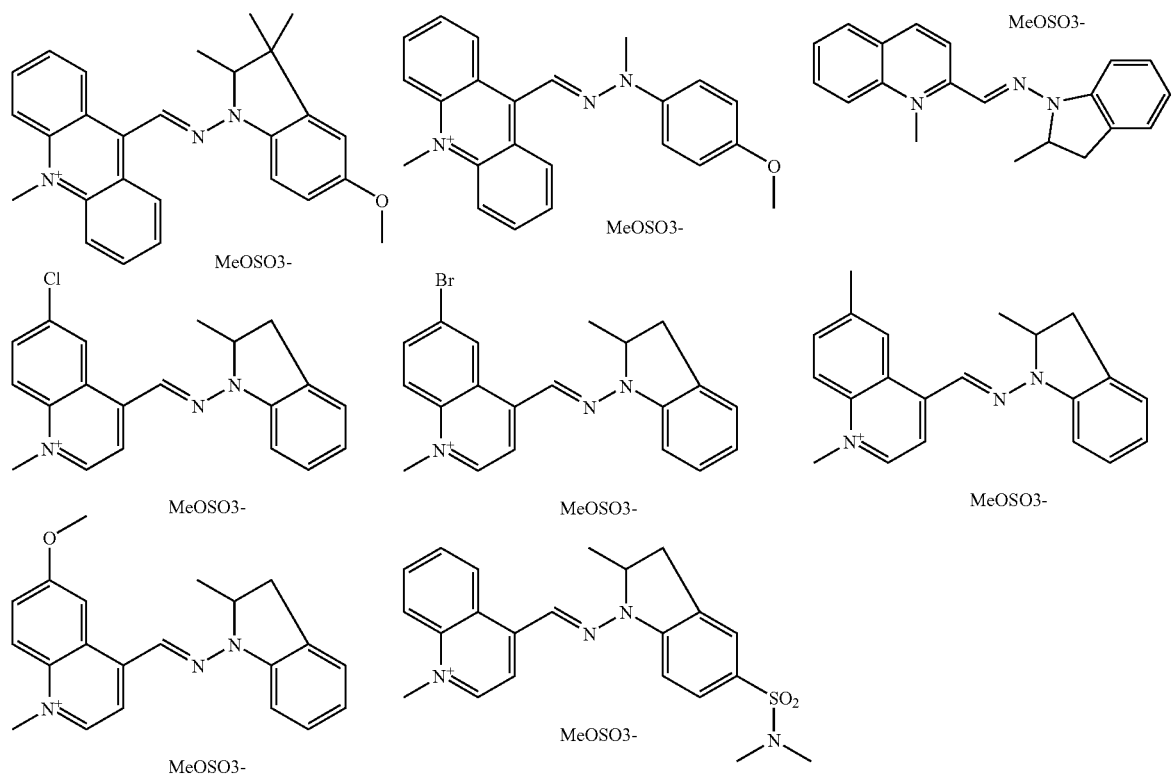
Other useful compounds are, for example, the quinolinium derivatives of formulae:
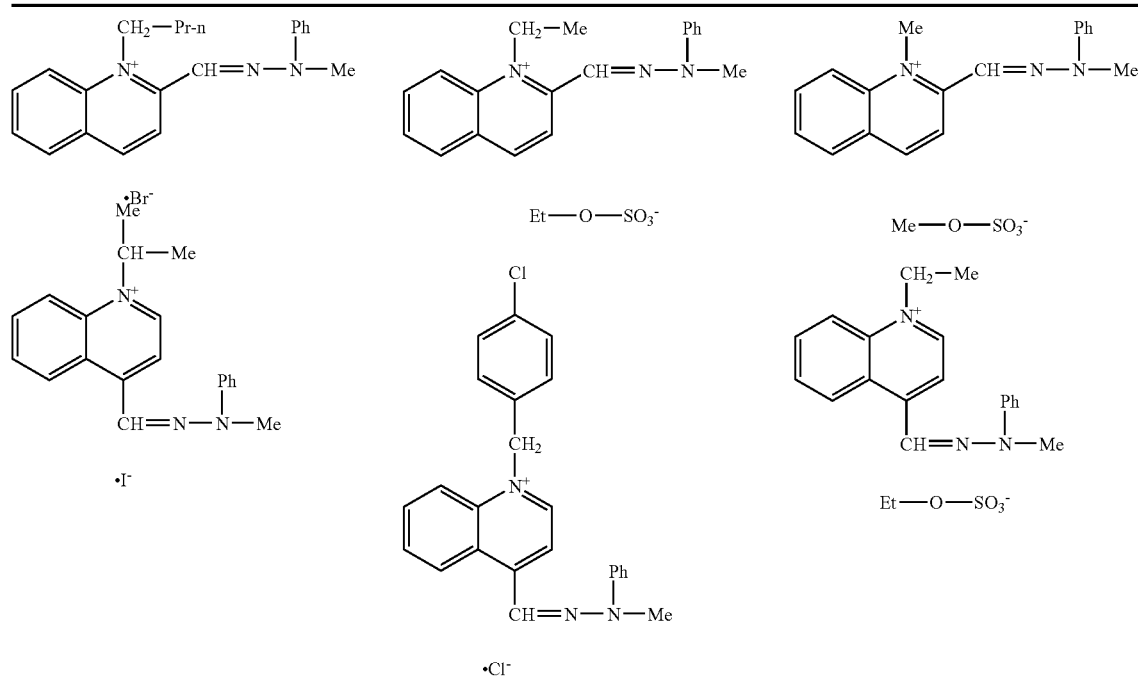

-continued

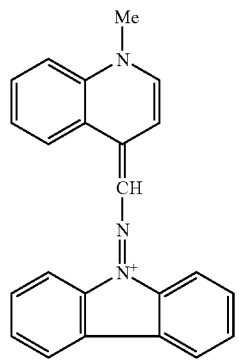

Me—O—SO₃⁻

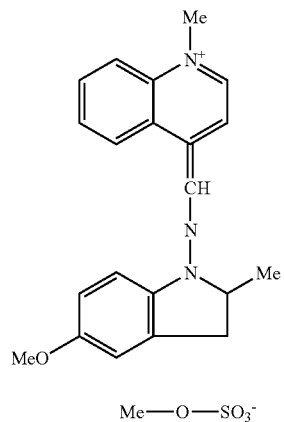

Me—O—SO₃⁻

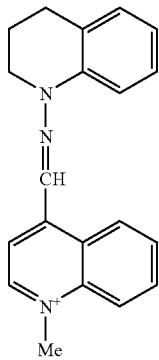

Me—O—SO₃⁻

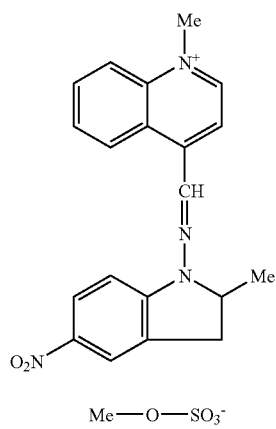

Me—O—SO₃⁻

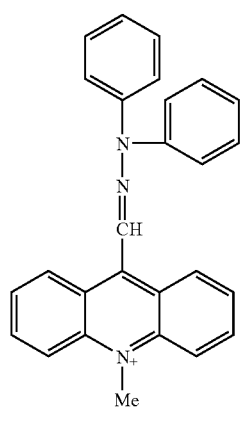

Me—O—SO₃⁻

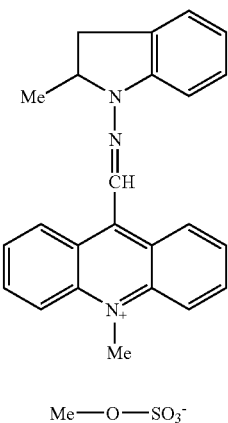

Me—O—SO₃⁻

Preferably, $R_7$ denotes $C_1$-$C_4$ alkyl or chlorobenzyl. $R_8$ denotes a hydrogen or halogen atom, a nitro radical, a $C_1$-$C_4$ alkoxy radical or a $C_1$-$C_4$ alkyl radical. $R_6$ and $R_5$ denote a hydrogen atom or form, together with the adjacent atoms, a benzene ring. $R_3$ preferably denotes a hydrogen atom, a $C_1$-$C_4$ alkoxy radical, a $C_1$-$C_4$ mono- or polyalkylsulfamoyl radical or a nitro group and $R_4$ denotes a hydrogen atom. $R_1$ denotes a $C_1$-$C_4$ alkyl radical or a phenyl radical or forms, with $R_2$, a 5- or 6-membered ring preferentially substituted with one or more $C_1$-$C_4$ alkyl radicals.

According to one particular embodiment, the compound of, formula (I) corresponds to the formula:

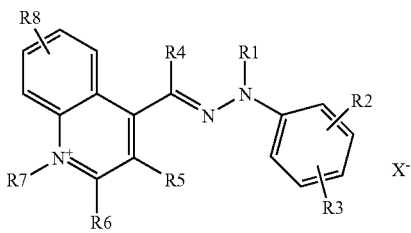

in which the radicals R1 to R7 are as defined above.

According to another particular embodiment, the compound of formula (I) corresponds to the formula:

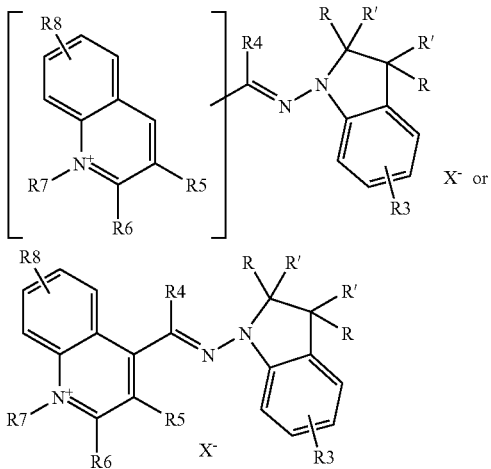

in which the radicals R1 to R7 are as defined above and R and R' are independently chosen from a hydrogen atom and a $C_1$-$C_4$ alkyl radical.

The concentration of direct dye(s) of formula (I) may range between 0.001% and 5% and preferably from about 0.05% to 2% by weight relative to the total weight of the dye composition.

The compositions of the invention preferably contain at least one cosmetic adjuvant chosen from monoalcohols such as alkanols, polyols, anionic, cationic, nonionic, amphoteric or zwitterionic surfactants, or mixtures thereof, mineral or organic thickeners, and in particular anionic, cationic, nonionic and amphoteric associative polymers.

The thickeners are especially chosen from the group consisting of:
(i) associative thickeners;
(ii) crosslinked acrylic acid homopolymers;
(iii) crosslinked copolymers of (meth)acrylic acid and of ($C_1$-$C_6$)alkyl acrylate;
(iv) nonionic homopolymers and copolymers containing ethylenically unsaturated monomers of ester and/or amide type;
(v) ammonium acrylate homopolymers or copolymers of ammonium acrylate and of acrylamide;
(vi) polysaccharides;
(vii) $C_{12}$-$C_{30}$ fatty alcohols;
(viii) mineral thickeners.

According to the invention, the expression "associative thickener" means an amphiphilic thickener comprising both hydrophilic units and hydrophobic units in particular comprising at least one $C_8$-$C_{30}$ fatty chain and at least one hydrophilic unit.

Associative thickeners according to the invention that may be used are associative polymers chosen from:
(a) nonionic amphiphilic polymers comprising at least one fatty chain and at least one hydrophilic unit;
(b) anionic amphiphilic polymers comprising at least one hydrophilic unit and at least one fatty-chain unit;
(c) cationic amphiphilic polymers comprising at least one hydrophilic unit and at least one fatty-chain unit;
(d) amphoteric amphiphilic polymers comprising at least one hydrophilic unit and at least one fatty-chain unit;
the fatty chains containing from 10 to 30 carbon atoms.

The nonionic amphiphilic polymers (a) comprising at least one fatty chain and at least one hydrophilic unit are preferably chosen from:
(1) celluloses modified with groups comprising at least one fatty chain;
examples that may be mentioned include:
hydroxyethylcelluloses modified with groups comprising at least one fatty chain, such as alkyl, arylalkyl or alkylaryl groups, or mixtures thereof, and in which the alkyl groups are preferably $C_8$-$C_{22}$, such as the product Natrosol Plus Grade 330 CS ($C_{16}$ alkyls) sold by the company Aqualon, or the product Bermocoll EHM 100 sold by the company Berol Nobel,
those modified with polyalkylene glycol alkylphenyl ether groups, such as the product Amercell Polymer HM-1500 (polyethylene glycol (15) nonylphenyl ether) sold by the company Amerchol.
(2) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie.
(3) polyether urethanes comprising at least one fatty chain, such as $C_{10}$-$C_{30}$ alkyl or alkenyl groups, for instance the products Dapral T 210 and Dapral T 212 sold by the company Akzo or the products Aculyn 44 and Aculyn 46 sold by the company Rohm & Haas.
(4) copolymers of vinylpyrrolidone and of hydrophobic fatty-chain monomers;
examples that may be mentioned include:
the products Antaron V216 or Ganex V216 (vinylpyrrolidone/hexadecene copolymer) sold by the company I.S.P.,
the products Antaron V220 or Ganex V220 (vinylpyrrolidone/eicosene copolymer) sold by the company I.S.P.
(5) copolymers of $C_1$-$C_6$ alkyl acrylates or methacrylates and of amphiphilic monomers comprising at least one fatty chain, such as, for example, the oxyethylenated methyl methacrylate/stearyl acrylate copolymer sold by the company Goldschmidt under the name Antil 208.
(6) copolymers of hydrophilic acrylates or methacrylates and of hydrophobic monomers comprising at least one fatty chain, such as, for example, the polyethylene glycol methacrylate/lauryl methacrylate copolymer.

Among the anionic amphiphilic polymers (b) according to the invention comprising at least one hydrophilic unit and at least one fatty-chain unit, the ones that are preferred are those comprising at least one fatty-chain allyl ether unit and at least one hydrophilic unit consisting of an ethylenic unsaturated anionic monomer, more particularly a vinylcarboxylic acid and most particularly an acrylic acid, a methacrylic acid or mixtures thereof, the fatty-chain allyl ether unit corresponding to the monomer of formula (V) below:

$$CH_2=C(R1)CH_2OB_nR \quad (V)$$

in which $R_1$ denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing from 10 to 30 carbon atoms, preferably 10 to 24 carbon atoms and even more particularly from 12 to 18 carbon atoms.

A unit of formula (V) that is more particularly preferred according to the present invention is a unit in which $R_1$ denotes H, n is equal to 10 and R denotes a stearyl ($C_{18}$) radical.

Anionic amphiphilic polymers of this type are described and prepared, according to an emulsion polymerization process, in patent EP-0 216 479 B2.

Among these anionic amphiphilic polymers that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (V), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Ciba under the names Salcare SC 80 and Salcare SC 90, which are aqueous 30% emulsions of a crosslinked terpolymer of methacrylic acid, of ethyl acrylate and of steareth-10 allyl ether (40/50/10).

The anionic amphiphilic polymers can also be chosen from those comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid, which are used according to the invention, preferably chosen from those in which the hydrophilic unit of unsaturated olefinic carboxylic acid type corresponds to the monomer of formula (VI) below:

$$H_2C=\underset{\underset{R^1}{|}}{C}-\underset{\underset{O}{\|}}{C}-OH \quad (VI)$$

in which formula $R^1$ denotes H or $CH_3$ or $C_2H_5$, i.e. acrylic acid, methacrylic acid or ethacrylic acid units, and in which the hydrophobic unit of the type such as a ($C_{10}$-$C_{30}$) alkyl ester of an unsaturated carboxylic acid corresponds to the monomer of formula (VII) below:

$$H_2C=CR^1-CO-OR^2 \quad (VII)$$

in which formula $R^1$ denotes H or $CH_3$ or $C_2H_5$ (i.e. acrylate, methacrylate or ethacrylate units) and preferably H (acrylate units) or $CH_3$ (methacrylate units), $R^2$ denoting a $C_{10}$-$C_{30}$ and preferably $C_{12}$-$C_{22}$ alkyl radical.

($C_{10}$-$C_{30}$)Alkyl esters of unsaturated carboxylic acids in accordance with the invention comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. Nos. 3,915,921 and 4,509,949.

The anionic amphiphilic polymers that can be used in the context of the present invention may more particularly denote polymers formed from a mixture of monomers comprising:

(i) essentially acrylic acid, an ester of formula (VIII) below:

$$H_2C=CR^1-CO-OR^2 \quad (VIII)$$

in which $R^1$ denotes H or $CH_3$, $R^2$ denoting an alkyl radical containing from 12 to 22 carbon atoms, and a crosslinking agent, such as, for example, those consisting of from 95% to 60% by weight of acrylic acid (hydrophilic unit), 4% to 40% by weight of $C_{10}$-$C_{30}$ alkyl acrylate (hydrophobic unit), and 0% to 6% by weight of crosslinking polymerizable monomer, or 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer, (ii) essentially acrylic acid and lauryl methacrylate, such as the product formed from 66% by weight of acrylic acid and 34% by weight of lauryl methacrylate.

The said crosslinking agent is a monomer containing a group

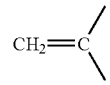

with at least one other polymerizable group whose unsaturated bonds are not conjugated. Mention may be made in particular of polyallyl ethers such as, in particular, polyallylsucrose and polyallylpentaerythritol.

Among the said polymers above, the ones most particularly preferred according to the present invention are the products sold by the company Goodrich under the trade names Pemulen TR1, Pemulen TR2, Carbopol 1382, and even more preferably Pemulen TR1, and the product sold by the company S.E.P.C. under the name Coatex SX.

As anionic amphiphilic fatty-chain polymers, mention may also be made of the ethoxylated copolymer of methacrylic acid/methyl acrylate/alkyl dimethyl-meta-isopropenylbenzylisocyanate sold under the name Viscophobe DB 1000 by the company Amerchol.

The cationic amphiphilic polymers (c) used in the present invention are preferably chosen from quaternized cellulose derivatives and polyacrylates containing amino side groups.

The quaternized cellulose derivatives are, in particular,
  quaternized celluloses modified with groups comprising at least one fatty chain, such as alkyl, arylalkyl or alkylaryl groups containing at least 8 carbon atoms, or mixtures thereof,
  quaternized hydroxyethylcelluloses modified with groups comprising at least one fatty chain, such as alkyl, arylalkyl or alkylaryl groups containing at least 8 carbon atoms, or mixtures thereof.

Quaternized or non-quaternized polyacrylates containing amino side groups, have, for example, hydrophobic groups, such as Steareth 20 (polyoxyethylenated(20) stearyl alcohol) or ($C_{10}$-$C_{30}$)alkyl PEG-20 itaconate.

The alkyl radicals borne by the above quaternized celluloses or hydroxyethylcelluloses preferably contain from 8 to 30 carbon atoms.

The aryl radicals preferably denote phenyl, benzyl, naphthyl or anthryl groups.

Examples of quaternized alkylhydroxyethylcelluloses containing $C_8$-$C_{30}$ fatty chains which may be indicated are the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Examples of polyacrylates containing amino side chains that may be mentioned are the polymers 8781-124B or 9492-103 or Structure Plus from the company National Starch.

As amphoteric amphiphilic polymers containing at least one fatty chain, mention may be made of copolymers of methacrylamidopropyltrimethylammonium chloride/acrylic acid/$C_{10}$-$C_{30}$ alkyl methacrylate, the alkyl radical preferably being a stearyl radical.

Preferably, the associative thickeners in the cosmetic compositions in accordance with the present invention advantageously have, in solution or in dispersion at a concentration of 1% active material in water, a viscosity, measured using a Rheomat RM 180 rheometer at 25° C., of greater than 0.1 ps and even more advantageously of greater than 0.2 cp, at a shear rate of 200 $s^{-1}$.

(ii) Among the crosslinked acrylic acid homopolymers that may be mentioned are those crosslinked with an allylic alcohol ether of the sugar series, such as, for example, the products sold under the names Carbopol 980, 981, 954, 2984 and 5984 by the company Goodrich or the products sold under the names Synthalen M and Synthalen K by the company 3 VSA.

(iii) Among the crosslinked copolymers of (meth)acrylic acid and of $C_1$-$C_6$ alkyl acrylate that may be mentioned is the product sold under the name Viscoatex 538C by the company Coatex, which is a crosslinked copolymer of methacrylic acid and of ethyl acrylate as an aqueous dispersion containing 38% active material, or the product sold under the name Aculyn 33 by the company Rohm & Haas, which is a crosslinked copolymer of acrylic acid and of ethyl acrylate as an aqueous dispersion containing 28% active material.

(iv) Among the nonionic homopolymers or copolymers containing ethylenically unsaturated monomers of ester and/or amide type, mention may be made of the products sold under the names: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); BPA 500 by the company Kobo (polymethyl methacrylate).

(v) Among the ammonium acrylate homopolymers that may be mentioned is the product sold under the name Microsap PAS 5193 by the company Hoechst.

Among the copolymers of ammonium acrylate and of acrylamide that may be mentioned is the product sold under the name Bozepol C Nouveau or the product PAS 5193 sold by the company Hoechst (which are described and prepared in documents FR-2 416 723, U.S. Pat. No. 2,798,053 and U.S. Pat. No. 2,923,692).

(vi) The thickening polysaccharides are especially chosen from glucans, modified or unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethylhydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans such as guar gums and nonionic derivatives thereof (hydroxypropyl guar) and xanthan gums, and mixtures thereof.

In general, the compounds of this type that may be used in the present invention are chosen from those described especially in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums—Polysaccharides and their Derivatives", edited by Roy L. Whistler, Second Edition, published by Academic Press Inc., the content of these three publications being entirely included in the present patent application by way of reference.

Starches, guar gums and celluloses and derivatives thereof will preferably be used.

The guar gums can be modified or unmodified.

The unmodified guar gums are, for example, the products sold under the name Vidogum GH 175 by the company Unipectine and under the names Meypro-Guar 50 and Jaguar C by the company Meyhall.

The modified nonionic guar gums are especially modified with $C_1$-$C_6$ hydroxyalkyl groups.

Among the hydroxyalkyl groups that may be mentioned, for example, are hydroxymethyl, hydroxyethyl, hydroxypropyl and hydroxybutyl groups.

These guar gums are well known in the prior art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, preferably ranges from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie (Meyhall) or under the name Galactasol 4H4FD2 by the company Aqualon.

Among the celluloses that are especially used are hydroxyethylcelluloses and hydroxypropylcelluloses. Mention may be made of the products sold under the names Klucel EF, Klucel H, Klucel LHF, Klucel MF and Klucel G by the company Aqualon.

The fatty alcohols are especially chosen from myristyl alcohol, cetyl alcohol, stearyl alcohol and behenyl alcohol.

The mineral thickeners (viii) are especially chosen from clays.

According to the invention, the thickener(s) may represent from 0.001% to 20% by weight, preferably from 0.01% to 10% by weight and more particularly from 0.1% to 3% by weight, relative to the total weight of the final composition.

The compositions of the invention also advantageously contain at least one surfactant, which is generally present in an amount of between 0.1% and 60% by weight approximately, preferably between 0.5% and 40% and even more preferentially between 1% and 30%, relative to the total weight of the composition.

This surfactant may be chosen from anionic, amphoteric, nonionic and cationic surfactants, or mixtures thereof.

The surfactants that are suitable for carrying out the present invention are especially the following:

(i) Anionic Surfactant(s):

As examples of anionic surfactants which can be used, alone or as mixtures, in the context of the present invention, mention may be made in particular (non-limiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all of these various compounds preferably containing from 8 to 24 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, in particular those containing from 2 to 50 ethylene oxide groups, and mixtures thereof.

Among the anionic surfactants, it is preferred according to the invention to use alkyl sulfate salts and alkyl ether sulfate salts and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and, in the context of the present invention, their nature is not a critical feature. Thus, they can be chosen in particular from (non-limiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It will be noted that the alkylpolyglycosides constitute nonionic surfactants that are particularly suitable in the context of the present invention.

(iii) Amphoteric Surfactant(s):

The amphoteric surfactants, whose nature is not a critical feature in the context of the present invention, can be, in particular (non-limiting list), aliphatic secondary or tertiary amine derivatives in which the aliphatic radical is a linear or branched chain containing 8 to 22 carbon atoms and containing at least one water-soluble anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido-($C_1$-$C_6$)alkylbetaines or ($C_8$-$C_{20}$)alkylamido ($C_1$-$C_6$)alkyl-sulfobetaines.

Among the amine derivatives, mention may be made of the products sold under the name Miranol, as described in U.S. Pat. Nos. 2,528,378 and 2,781,354 and having the structures:

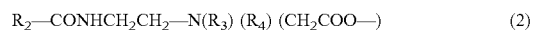

$$R_2—CONHCH_2CH_2—N(R_3)(R_4)(CH_2COO—) \quad (2)$$

in which: $R_2$ denotes a linear or branched $C_5$-$C_{20}$ alkyl radical derived from an acid $R_2$—COOH present in hydrolysed coconut oil, a heptyl, nonyl or undecyl radical, $R_3$ denotes a β-hydroxyethyl group and $R_4$ denotes a carboxymethyl group;

and

$$R_5—CONHCH_2CH_2—N(B)(C) \quad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_5$ denotes a linear or branched, saturated or unsaturated $C_5$-$C_{20}$ alkyl radical of an acid $R_5$—COOH present in, for example, coconut oil or in hydrolysed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caproamphodipropionate, lauroamphodipropionic acid, cocoamphodipropionic acid.

By way of example, mention may be made of the cocoamphodiacetate sold under the trade name Miranol C2M Concentrate by the company Rhodia Chimie.

(iv) Cationic Surfactant(s):

The cationic surfactants may be chosen from: A) the quaternary ammonium salts of general formula (XII) below:

(XII)

in which $X^-$ is an anion chosen from the group of halides (chloride, bromide or iodide) or ($C_2$-$C_6$)alkyl sulfates, more particularly methyl sulfate, phosphates, alkyl or alkylaryl sulfonates, anions derived from organic acid, such as acetate or lactate, and i) the radicals $R_1$ to $R_3$, which may be identical or different, represent a linear or branched aliphatic radical containing from 1 to 4 carbon atoms, or an aromatic radical such as aryl or alkylaryl. The aliphatic radicals can comprise heteroatoms such as, in particular, oxygen, nitrogen, sulfur or halogens. The aliphatic radicals are chosen, for example, from alkyl, alkoxy and alkylamide radicals.

$R_4$ denotes a linear or branched alkyl radical containing from 16 to 30 carbon atoms.

The cationic surfactant is preferably a behenyltrimethylammonium salt (for example chloride).

ii) the radicals $R_1$ and $R_2$, which may be identical or different, represent a linear or branched aliphatic radical containing from 1 to 4 carbon atoms, or an aromatic radical such as aryl or alkylaryl. The aliphatic radicals can comprise heteroatoms such as, in particular, oxygen, nitrogen, sulfur or halogens. The aliphatic radicals are chosen, for example, from alkyl, alkoxy, alkylamide and hydroxyalkyl radicals containing from about 1 to 4 carbon atoms;

$R_3$ and $R_4$, which may be identical or different, denote a linear or branched alkyl radical containing from 12 to 30 carbon atoms, the said radical comprising at least one ester or amide function.

$R_3$ and $R_4$ are chosen in particular from $(C_{12}\text{-}C_{22})$alkylamido$(C_2\text{-}C_6)$alkyl and $(C_{12}\text{-}C_{22})$alkylacetate radicals.

The cationic surfactant is preferably a stearamidopropyldimethyl(myristyl acetate)ammonium salt (for example chloride);

B)—the quaternary ammonium salts of imidazolinium, such as, for example, that of formula (XIII) below:

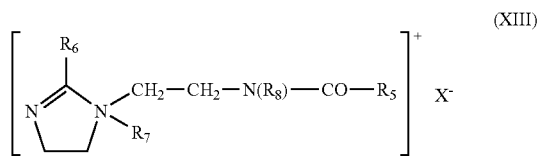

in which $R_5$ represents an alkenyl or alkyl radical containing from 8 to 30 carbon atoms, for example fatty acid derivatives of tallow, $R_6$ represents a hydrogen atom, a $C_1\text{-}C_4$ alkyl radical or an alkenyl or alkyl radical containing from 8 to 30 carbon atoms, $R_7$ represents a $C_1\text{-}C_4$ alkyl radical, $R_8$ represents a hydrogen atom or a $C_1\text{-}C_4$ alkyl radical, and X is an anion chosen from the group of halides, phosphates, acetates, lactates, alkyl sulfates, alkyl sulfonates or alkylaryl sulfonates. $R_5$ and $R_6$ preferably denote a mixture of alkenyl or alkyl radicals containing from 12 to 21 carbon atoms, such as, for example, fatty acid derivatives of tallow, $R_7$ denotes methyl and $R_8$ denotes hydrogen. Such a product is, for example, Quaternium-27 (CTFA 1997) or Quaternium-83 (CTFA 1997), which are sold under the names "Rewoquat" W75, W90, W75PG and W75HPG by the company Witco, C)—the diquaternary ammonium salts of formula (XIV):

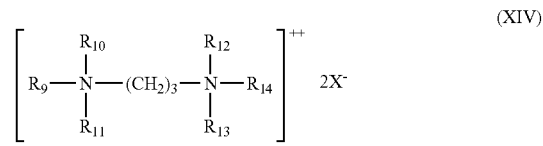

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen and an alkyl radical containing from 1 to 4 carbon atoms, and X is an anion chosen from the group of halides, acetates, phosphates, nitrates and methyl sulfates. Such diquaternary ammonium salts in particular comprise propanetallowdiammonium dichloride;

D)—the quaternary ammonium salts containing at least one ester function, of formula (XV) below:

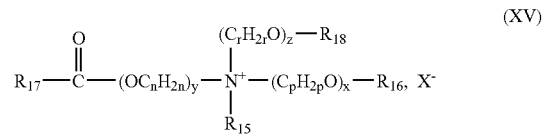

in which:

$R_{15}$ is chosen from $C_1\text{-}C_6$ alkyl radicals and $C_1\text{-}C_6$ hydroxyalkyl or dihydroxyalkyl radicals;

$R_{16}$ is chosen from:

a radical

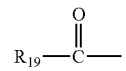

linear or branched, saturated or unsaturated $C_1\text{-}C_{22}$ hydrocarbon-based radicals $R_{20}$, a hydrogen atom, $R_{18}$ is chosen from:

a radical

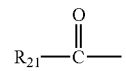

linear or branched, saturated or unsaturated $C_1\text{-}C_6$ hydrocarbon-based radicals $R_{22}$, a hydrogen atom, $R_{17}$, $R_{19}$ and $R_{21}$, which may be identical or different, are chosen from linear or branched, saturated or unsaturated $C_7\text{-}C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z is from 1 to 15, that when x is 0, then $R_{16}$ denotes $R_{20}$ and that when z is 0, then $R_{18}$ denotes $R_{22}$.

Use is made more particularly of the ammonium salts of formula (XV) in which:
R$_{15}$ denotes a methyl or ethyl radical,
x and y are equal to 1;
z is equal to 0 or 1;
n, p and r are equal to 2;
R$_{16}$ is chosen from:
a radical

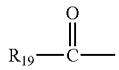

methyl, ethyl or C$_{14}$-C$_{22}$ hydrocarbon-based radicals,
a hydrogen atom;
R$_{17}$, R$_{19}$ and R$_{21}$, which may be identical or different, are chosen from linear or branched, saturated or unsaturated C$_7$-C$_{21}$ hydrocarbon-based radicals;
R$_{18}$ is chosen from:
a radical

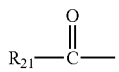

a hydrogen atom.

Such compounds are sold, for example, under the names Dehyquart by the company Cognis, Stepanquat by the company Stepan, Noxamium by the company Ceca, and Rewoquat WE 18 by the company Rewo-Witco.

Among the quaternary ammonium salts that are preferred are behenyltrimethylammonium chloride and stearamidopropyldimethyl(myristyl acetate)ammonium chloride, sold under the name "Ceraphyl 70" by the company Van Dyk, and Quaternium-27 or Quaternium-83 sold by the company Witco.

It is preferred to use an anionic surfactant chosen from sodium, triethanolamine or ammonium (C$_{12}$-C$_{14}$)alkyl sulfates, sodium, triethanolamine or ammonium (C$_{12}$-C$_{14}$)alkyl ether sulfates oxyethylenated with 2.2 mol of ethylene oxide, sodium cocoyl isethionate and sodium α-(C$_{14}$-C$_{16}$) olefin sulfonate, and mixtures thereof, with:
  either an amphoteric surfactant such as the amine derivatives known as disodium cocoamphodipropionate or sodium cocoamphopropionate sold especially by the company Rhodia Chimie under the trade name "Miranol® C2M CONC" as an aqueous solution containing 38% active material, or under the name Miranol® C32;
  or an amphoteric surfactant such as alkylbetaines, in particular the cocobetaine sold under the name "Dehyton® AB 30" as an aqueous solution containing 32% AM by the company Cognis, or (C$_8$-C$_{20}$)alkylamido (C$_1$-C$_6$)alkylbetaines, in particular Tegobetaine® F50 sold by the company Goldschmidt.

The preferred alkanols are linear or branched C$_1$-C$_4$ alkanols and in particular ethanol and isopropanol.

The polyols preferably have a molecular mass of less than 1000. They may be linear or branched and may contain between 2 and 10 hydroxyl functions. Among these polyols, mention may be made of propylene glycol, glycerol, hexylene glycol, neopentyl glycol, isoprene glycol, 1,4-butanediol, 2-methyl-1,3-propanediol and polyethylene glycols.

The alkanols or polyols described above are generally present in an amount for each one of between 0.1% and 30% by weight and preferably between 1% and 20% by weight relative to the weight of the composition.

The dye composition in accordance with the invention may also contain additional direct dyes other than those of formula (I), which may be chosen especially from neutral, acidic or cationic nitrobenzene direct dyes, neutral, acidic or cationic azo direct dyes, quinone direct dyes and in particular neutral, acidic or cationic anthraquinone direct dyes, azine direct dyes, methine direct dyes, triarylmethane direct dyes, indoamine direct dyes and natural direct dyes.

Among the benzenic direct dyes, mention may be made in particular of the following compounds:
  1,4-diamino-2-nitrobenzene
  1-amino-2-nitro-4-(β-hydroxyethylamino)benzene
  1-amino-2-nitro-4-bis(β-hydroxyethyl)aminobenzene
  1,4-bis(β-hydroxyethylamino)-2-nitrobenzene
  1-β-hydroxyethylamino-2-nitro-4-bis(β-hydroxyethylamino)benzene
  1-β-hydroxyethylamino-2-nitro-4-aminobenzene
  1-β-hydroxyethylamino-2-nitro-4-(ethyl) (β-hydroxyethyl)aminobenzene
  1-amino-3-methyl-4-β-hydroxyethylamino-6-nitrobenzene
  1-amino-2-nitro-4-β-hydroxyethylamino-5-chlorobenzene
  1,2-diamino-4-nitrobenzene
  1-amino-2-β-hydroxyethylamino-5-nitrobenzene
  1,2-bis(β-hydroxyethylamino)-4-nitrobenzene
  1-amino-2-[tris(hydroxymethyl)methylamino]-5-nitrobenzene
  1-hydroxy-2-amino-5-nitrobenzene
  1-hydroxy-2-amino-4-nitrobenzene
  1-hydroxy-3-nitro-4-aminobenzene
  1-hydroxy-2-amino-4,6-dinitrobenzene
  1-β-hydroxyethyloxy-2-β-hydroxyethylamino-5-nitrobenzene
  1-methoxy-2-β-hydroxyethylamino-5-nitrobenzene
  1-β-hydroxyethyloxy-3-methylamino-4-nitrobenzene
  1-β,γ-dihydroxypropyloxy-3-methylamino-4-nitrobenzene
  1-β-hydroxyethylamino-4-β,γ-dihydroxypropyloxy-2-nitrobenzene
  1-β,γ-dihydroxypropylamino-4-trifluoromethyl-2-nitrobenzene
  1-β-hydroxyethylamino-4-trifluoromethyl-2-nitrobenzene
  1-β-hydroxyethylamino-3-methyl-2-nitrobenzene
  1-β-aminoethylamino-5-methoxy-2-nitrobenzene
  1-hydroxy-2-chloro-6-ethylamino-4-nitrobenzene
  1-hydroxy-2-chloro-6-amino-4-nitrobenzene
  1-hydroxy-6-[bis(β-hydroxyethyl)amino]-3-nitrobenzene
  1-β-hydroxyethylamino-2-nitrobenzene
  1-hydroxy-4-β-hydroxyethylamino-3-nitrobenzene.

Among the azo direct dyes that may be mentioned are the cationic azo dyes described in patent applications WO 95/15144, WO 95/01772, EP 714 954, and WO 01/66646, the content of which forms an integral part of the invention.

Among these compounds, mention may be made most particularly of the following dyes:
  1,3-dimethyl-2-[[4-(dimethylamino)phenyl]azo]-1H-imidazolium chloride,
  1,3-dimethyl-2-[(4-aminophenyl)azo]-1H-imidazolium chloride,
  1-methyl-4-[(methylphenylhydrazono)methyl]pyridinium methyl sulfate.

Among the azo direct dyes that may also be mentioned are the following dyes described in the Colour Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
  1-N-methylmorpholiniumpropylamino-4-hydroxyanthraquinone
  1-aminopropylamino-4-methylaminoanthraquinone
  1-aminopropylaminoanthraquinone
  5-β-hydroxyethyl-1,4-diaminoanthraquinone
  2-aminoethylaminoanthraquinone
  1,4-bis(β,γ-dihydroxypropylamino)anthraquinone.

Among the azine dyes that may be mentioned are the following compounds:
Basic Blue 17
Basic Red 2.

Among the triarylmethane dyes, mention may be made of the following compounds:
Basic Green 1
Acid Blue 9
Basic Violet 3
Basic Violet 14
Basic Blue 7
Acid Violet 49
Basic Blue 26
Acid Blue 7.

Among the indoamine dyes, mention may be made of the following compounds:
  2-β-hydroxyethylamino-5-[bis(β-4'-hydroxyethyl)amino]anilino-1,4-benzoquinone;
  2-β-hydroxyethylamino-5-(2'-methoxy-4'-amino)anilino-1,4-benzoquinone;
  3-N(2'-chloro-4'-hydroxy)phenylacetylamino-6-methoxy-1,4-benzoquinoneimine;
  3-N(3'-chloro-4'-methylamino)phenylureido-6-methyl-1,4-benzoquinoneimine;
  3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The total proportion of additional direct dyes is preferably from 0.001% to 20% by weight approximately, and even more preferably from 0.005% to 10% by weight approximately, relative to the total weight of the composition.

The composition of the invention may also comprise an oxidizing agent. This oxidizing agent may be any oxidizing agent conventionally used for bleaching human keratin fibres. The oxidizing agent is preferably chosen from hydrogen peroxide, urea peroxide, alkali metal bromates, persalts such as perborates and persulfates, peracids and enzymes, among which mention may be made of peroxidases, 2-electron oxidoreductases such as uricases, and 4-electron oxygenases such as laccases. The use of hydrogen peroxide is particularly preferred.

When the composition according to the invention is intended for standard oxidation dyeing, it also comprises an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines that may be mentioned, more particularly are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxy-propyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylamino-ethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diamino-phenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives that can be mentioned are the compounds described, for example, in patents DE 2 359 399; JP 88-169 571; JP 05-163 124; EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]-pyrimidine-3,7-diamine, 2,5,N7,N7-tetramethylpyrazolo-[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives that may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The composition according to the invention may also contain one or more couplers conventionally used for standard oxidation dyeing of human keratin fibres. Among these couplers, mention may be made especially of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the addition salts thereof with an acid.

In the composition of the present invention, the coupler(s) is (are) generally present in an amount ranging from 0.001% to 10% by weight approximately, and more preferably from 0.005% to 6% by weight, relative to the total weight of the dye composition. The oxidation base(s) is (are) present in an amount preferably ranging from 0.001% to 10% by weight approximately, and more preferably from 0.005% to 6% by weight, relative to the total weight of the dye composition.

In general, the addition salts with an acid that may be used in the context of the dye compositions of the invention for the oxidation bases and couplers are chosen especially from the hydrochlorides, hydrobromides, sulfates, citrates, succinates, tartrates, lactates, tosylates, benzenesulfonates, phosphates and acetates.

Needless to say, a person skilled in the art will take care to select the optional additional compound(s) such that the advantageous properties intrinsically associated with the dye composition in accordance with the invention are not, or are not substantially, adversely affected by the addition(s) envisaged.

The pH of the dye composition in accordance with the invention is generally between about 3 and 12 and preferably between about 5 and 11. It may be adjusted to the desired value using acidifying or basifying agents usually used in the dyeing of keratin fibres, or alternatively using standard buffer systems.

Among the acidifying agents that may be mentioned, for example, are mineral or organic acids such as hydrochloric acid, orthophosphoric acid, sulfuric acid, carboxylic acids such as acetic acid, tartaric acid, citric acid and lactic acid, and sulfonic acids.

Among the basifying agents that may be mentioned, for example, are aqueous ammonia, alkaline carbonates, alkanolamines such as mono-, di- and triethanolamine and derivatives thereof, sodium hydroxide, potassium hydroxide and the compounds of formula (XVI) below:

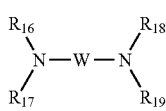

(XVI)

in which W is a propylene residue that is unsubstituted or substituted with a hydroxyl group or a $C_1$-$C_4$ alkyl radical; $R_{16}$, $R_{17}$, $R_{18}$ and $R_{19}$, which may be identical or different, represent a hydrogen atom, a $C_1$-$C_4$ alkyl radical or a $C_1$-$C_4$ hydroxyalkyl radical.

The dye composition in accordance with the invention may also contain various adjuvants conventionally used in hair dye compositions, such as antioxidants, penetrants, sequestrants, fragrances, buffers, dispersants, anionic, cationic, nonionic, amphoteric or zwitterionic polymers or mixtures thereof, conditioning agents such as silicones, which may be volatile or non-volatile and modified or unmodified, film-forming agents, fatty substances including ceramides and fatty alcohols, preserving agents, opacifiers, and anionic, cationic, nonionic, amphoteric or zwitterionic polymers and mixtures thereof.

The dye composition according to the invention may be in various forms, such as in the form of liquids, creams or gels, or in any other form that is suitable for dyeing human keratin fibres, and especially human hair.

A subject of the invention is also a process of direct dyeing, which comprises the application of a dye composition comprising a dye of formula (I) as defined above to human keratin fibres. After a leave-in time, the fibres are rinsed.

A subject of the invention is also a process of oxidation dyeing, which comprises the application to the human keratin fibres of a dye composition comprising a dye of formula (I), at least one oxidation base and optionally at least one coupler, in the presence of an oxidizing agent.

The oxidation base, the coupler and the oxidizing agent are as defined above.

In the case of oxidation dyeing or lightening direct dyeing, the dye composition is mixed, preferably at the time of use, with a composition containing, in a medium that is suitable for dyeing, at least one oxidizing agent, this oxidizing agent being present in an amount that is sufficient to develop a coloration. The mixture obtained is then applied to the fibres. After a leave-in time of 3 to 50 minutes approximately and preferably 5 to 30 minutes approximately, the fibres are rinsed, washed with shampoo, rinsed again and then dried.

The oxidizing composition may also contain various adjuvants conventionally used in compositions for dyeing the hair, and as defined above.

The pH of the oxidizing composition containing the oxidizing agent is such that, after mixing with the dye composition, the pH of the resulting composition applied to the keratin fibres preferably ranges from 3 to 12 approximately, and even more preferably between 5 and 11. It may be adjusted to the desired value by means of acidifying or basifying agents usually used in the dyeing of human keratin fibres, and as defined above.

The composition that is finally applied to the fibres may be in various forms, such as in the form of liquids, creams or gels or in any other form that is suitable for dyeing human keratin fibres, and especially the hair.

Another subject of the invention is a multi-compartment device or "kit", preferably a two-compartment device, for dyeing human keratin fibres, and more particularly the hair, in which a first compartment contains the dye composition of the invention containing at least one dye of formula (I) and a second compartment contains the oxidizing composition. This device may be equipped with a means for applying the desired mixture to the hair, such as the devices described in patent FR-2 586 913 in the name of the Applicant.

The examples that follow, of dye compositions, are intended to illustrate the invention without being limiting in nature.

The examples will be given later.

EXAMPLES

The dye compositions below according to the invention are prepared.

| Composition 1 | |
|---|---|
| Compound 1 | 0.5 g |
| Hydroxyethylcellulose | 1.0 g |
| Ethanol | 5 g |
| 2-Amino-2-methylpropanol | qs pH 8 |
| Water | qs 100 g |
| Composition 2 | |
| Compound 13 | 0.4 g |
| Hydroxypropyl guar | 1.5 g |
| Propylene glycol | 7 g |
| Decylglucoside | 4 g AM |
| 2-Amino-2-methylpropanol | qs pH 9 |
| Water | qs 100 g |

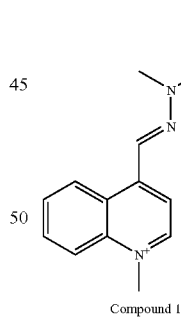

Compound 1

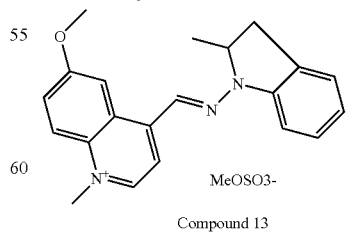

Compound 13

When composition 1 is applied to keratin fibres for 20 minutes at room temperature, followed by rinsing, an orange-yellow coloration is obtained.

When composition 2 is applied to keratin fibres for 20 minutes at room temperature, followed by rinsing, a blue-red coloration is obtained.

| Composition 3 | |
|---|---|
| Compound 1 | 0.5 |
| Oleyl alcohol polyglycerolated with 2 mol of glycerol | 4 |
| Oleyl alcohol polyglycerolated with 4 mol of glycerol | 5.69 AM |
| Oleic acid | 3 |
| Oleylamine containing 2 mol of ethylene oxide, sold under the trade name Ethomeen 012 by the company Akzo | 7 |
| Diethylaminopropyl laurylaminosuccinamate, sodium salt, containing 55% AM | 3.0 AM |
| Oleyl alcohol | 5 |
| Oleic acid diethanolamide | 12 |
| Ethyl alcohol | 7 |
| Propylene glycol | 3.5 |
| Dipropylene glycol | 0.5 |
| Propylene glycol monomethyl ether | 9 |
| Antioxidant/sequestrant | qs |
| Ammonium acetate | 0.8 |
| Sodium metabisulfite as an aqueous 35% solution | 0.455 |
| 20% aqueous ammonia | 10 |
| Water | qs 100 g |

At the time of use, composition 3 is mixed with the 20-V oxidizing agent (weight-for-weight) and is then applied at room temperature to two types of hair: natural 90% grey (NG) hair and permanent-waved grey (PWG) hair. The leave-in time is 20 minutes.

After the 20 minutes of application, the locks are rinsed and then shampooed (Elsève® Multivitamin shampoo).

After drying, the colour of the locks was evaluated before and after exposure to light in the L*a*b* system, using a Minolta CM 2002® spectrophotometer (illuminant D65). In this L*a*b* system, L* represents the intensity of the colour, a* indicates the green/red colour axis and b* indicates the blue/yellow colour axis. The smaller the value of L, the darker or more intense the colour. The greater the value of a*, the redder the shade, and the greater the value of b*, the bluer the shade.

As shown by the tables below, composition 3 allows a very chromatic orange-yellow coloration to be obtained, which practically does not vary as a function of the nature of the hair.

| | L* | a* | b* |
|---|---|---|---|
| NG after coloration | 61.06 | 7.28 | 53.37 |
| PWG after coloration | 58.84 | 8.74 | 56.48 |

What is claimed is:

1. A process for dyeing human keratin fibers, comprising applying to said fibers a composition comprising, in a suitable medium, at least one direct cationic hydrazone dye of formula (I), or a tautomeric form thereof:

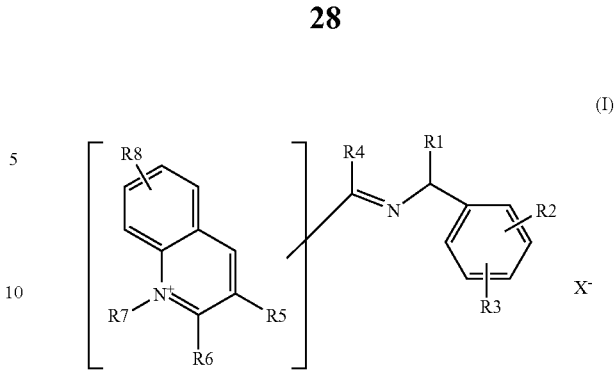

wherein $R_1$ and $R_7$ are, independently of each other, chosen from $C_1$-$C_6$ alkyl, $C_1$-$C_6$ hydroxyalkyl, benzyl, p-chlorobenzyl and phenyl radicals, $R_4$ is chosen from a hydrogen atom and $C_1$-$C_6$ alkyl radicals, $R_2$, $R_3$, $R_5$, $R_6$ and $R_8$ are, independently of each other, chosen from hydrogen atoms, $C_1$-$C_6$ alkyl radicals, halogen atoms, nitro radicals, $C_1$-$C_6$ alkoxy radicals, amino radicals, $C_1$-$C_6$ alkylamino radicals, $C_1$-$C_6$ dialkylamino radicals, sulfamoyl radicals, $C_1$-$C_6$ dialkylsulfamoyl radicals, $C_1$-$C_6$ dihydroxyalkylamino radicals and $C_1$-$C_6$ dihydroxyalkylamino radicals, $R_1$ may form, with $R_2$ or $R_3$ and the atoms to which they are attached, a saturated or unsaturated, 5-, 6- or 7-membered ring optionally substituted with at least one $C_1$-$C_6$ alkyl radical, or optionally fused with a benzene nucleus, $R_1$ and $R_4$ may form, together with the atoms to which they are attached, a 5-, 6- or 7-membered unsaturated ring, $R_5$ and $R_6$ may form, together with the atoms to which they are attached, a saturated or unsaturated 5-, 6- or 7-membered ring, wherein the bonding between the hydrazone group and the quinoline group takes place on any of the atoms of the quinoline heterocycle, and X⁻ is an anion that ensures the neutrality of the molecule.

2. The process of claim 1, wherein the bonding between the hydrazone group and the quinoline group takes place on the quinoline heterocycle at the positions of the groups R5, R6, and/or R7.

3. The process of claim 1, wherein R7 is a $C_1$-$C_4$ alkyl.

4. The process of claim 1, wherein $R_8$ is chosen from a hydrogen, a halogen atom, a nitro radical, a $C_1$-$C_4$ alkoxy radical and a $C_1$-$C_3$ alkyl radical.

5. The process of claim 1, wherein $R_6$ and $R_5$ are both hydrogen atoms or form, together with the atoms to which they are attached, a benzene ring.

6. The process of claim 1, wherein $R_3$ is chosen from a hydrogen atom, a $C_1$-$C_4$ alkoxy radical, a $C_1$-$C_4$ mono- or polyalkylsulfamoyl radical and a nitro group.

7. The process of claim 1, wherein $R_4$ is a hydrogen atom.

8. The process of claim 1, wherein $R_1$ is chosen from a $C_1$-$C_4$ alkyl radical and a phenyl radical or forms, with $R_2$ and with the atoms to which are attached, a 5- or 6-membered ring.

9. The process of claim 8, wherein said 5- or 6-membered ring is substituted with a $C_1$-$C_4$ alkyl radical.

10. The process of claim 1, wherein the at least one compound of formula (I) is chosen from compounds of formula:

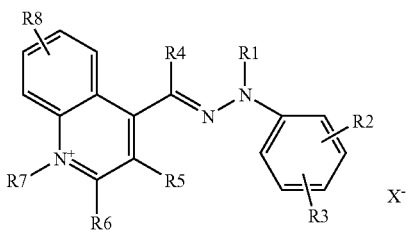

wherein
- $R_1$ and $R_7$ are, independently of each other, chosen from $C_1$-$C_6$ alkyl, $C_1$-$C_6$ hydroxyalkyl, benzyl, p-chlorobenzyl and phenyl radicals,
- $R_4$ is chosen from a hydrogen atom and $C_1$-$C_6$ alkyl radicals,
- $R_2$, $R_3$, $R_5$, $R_6$ and $R_8$ are, independently of each other, chosen from hydrogen atoms, $C_1$-$C_6$ alkyl radicals, halogen atoms, nitro radicals, $C_1$-$C_6$ alkoxy radicals, amino radicals, $C_1$-$C_6$ alkylamino radicals, $C_1$-$C_6$ dialkylamino radicals, sulfamoyl radicals, $C_1$-$C_6$ dialkylsulfamoyl radicals, $C_1$-$C_6$ dihydroxyalkylamino radicals and $C_1$-$C_6$ dihydroxyalkylamino radicals,
- $R_1$ may form, with $R_2$ or $R_3$ and the atoms to which they are attached, a saturated or unsaturated, 5-, 6- or 7-membered ring optionally substituted with at least one $C_1$-$C_6$ alkyl radical, or optionally fused with a benzene nucleus,
- $R_1$ and $R_4$ may form, together with the atoms to which they are attached, a 5-, 6- or 7-membered unsaturated ring,
- $R_5$ and $R_6$ may form, together with the atoms to which they are attached, a saturated or unsaturated 5-, 6- or 7-membered ring, wherein the bonding between the hydrazone group and the quinoline group takes place on any of the atoms of the quinoline heterocycle, and X⁻ is an anion that ensures the neutrality of the molecule.

11. The process of claim 1, wherein the at least one compound of formula (I) is chosen from the following formulas:

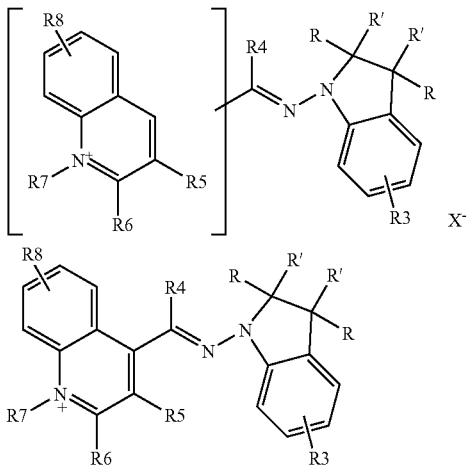

wherein R and R' are independently chosen from hydrogen atoms and $C_1$-$C_4$ alkyl radicals and wherein
- $R_1$ and $R_7$ are, independently of each other, chosen from $C_1$-$C_6$ alkyl, $C_1$-$C_6$ hydroxyalkyl, benzyl, p-chlorobenzyl and phenyl radicals,
- $R_4$ is chosen from a hydrogen atom and $C_1$-$C_6$ alkyl radicals,
- $R_2$, $R_3$, $R_5$, $R_6$ and $R_8$ are, independently of each other, chosen from hydrogen atoms, $C_1$-$C_6$ alkyl radicals, halogen atoms, nitro radicals, $C_1$-$C_6$ alkoxy radicals, amino radicals, $C_1$-$C_6$ alkylamino radicals, $C_1$-$C_6$ dialkylamino radicals, sulfamoyl radicals, $C_1$-$C_6$ dialkylsulfamoyl radicals, $C_1$-$C_6$ dihydroxyalkylamino radicals and $C_1$-$C_6$ dihydroxyalkylamino radicals,
- $R_1$ may form, with $R_2$ or $R_3$ and the atoms to which they are attached, a saturated or unsaturated, 5-, 6- or 7-membered ring optionally substituted with at least one $C_1$-$C_6$ alkyl radical, or optionally fused with a benzene nucleus,
- $R_1$ and $R_4$ may form, together with the atoms to which they are attached, a 5-, 6- or 7-membered unsaturated ring,
- $R_5$ and $R_6$ may form, together with the atoms to which they are attached, a saturated or unsaturated 5-, 6- or 7-membered ring, wherein the bonding between the hydrazone group and the quinoline group takes place on any of the atoms of the quinoline heterocycle, and X⁻ is an anion that ensures the neutrality of the molecule.

12. The process of claim 10, wherein the bonding between the hydrazone group and the quinoline group takes place on the quinoline heterocycle at the positions of the groups R5, R6, and/or R7.

13. The process of claim 1, in which the at least one compound of formula (I) is chosen from the following compounds:

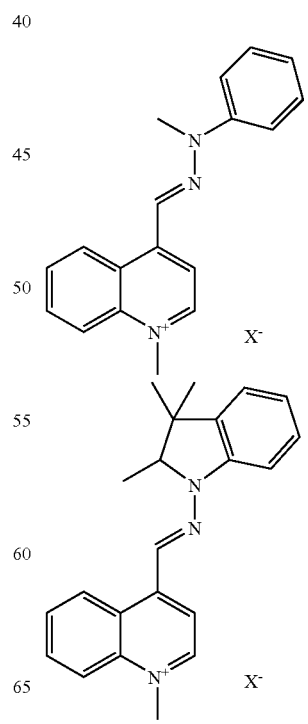

-continued
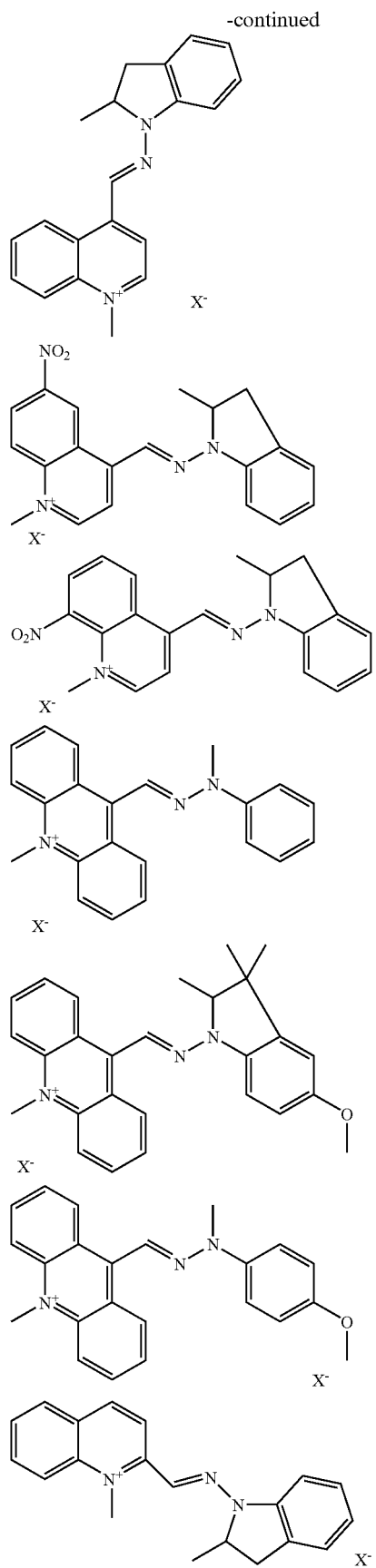
-continued
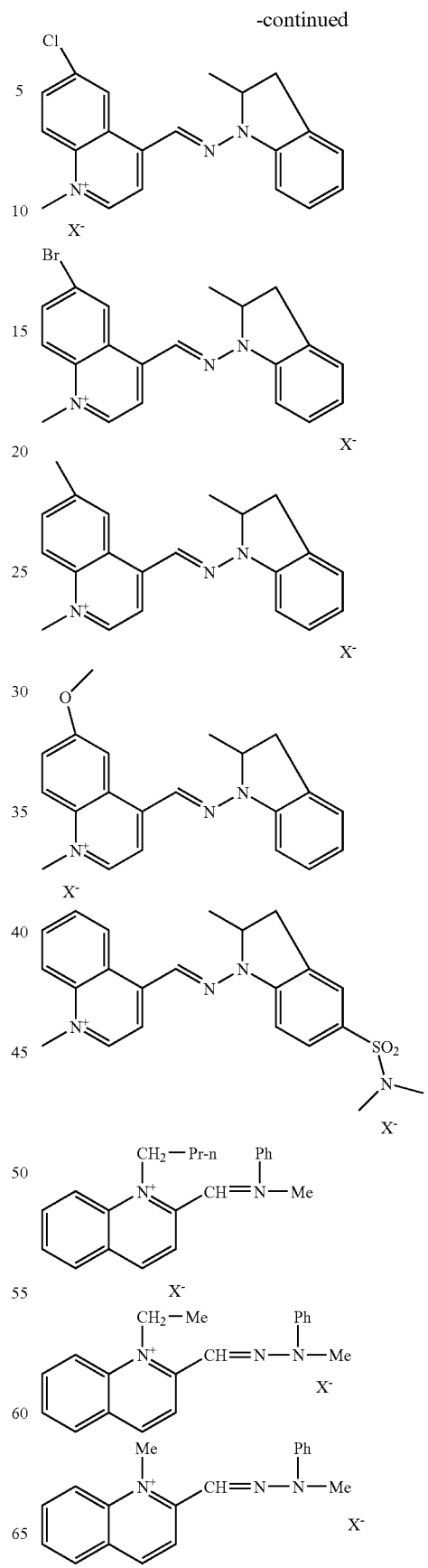

-continued
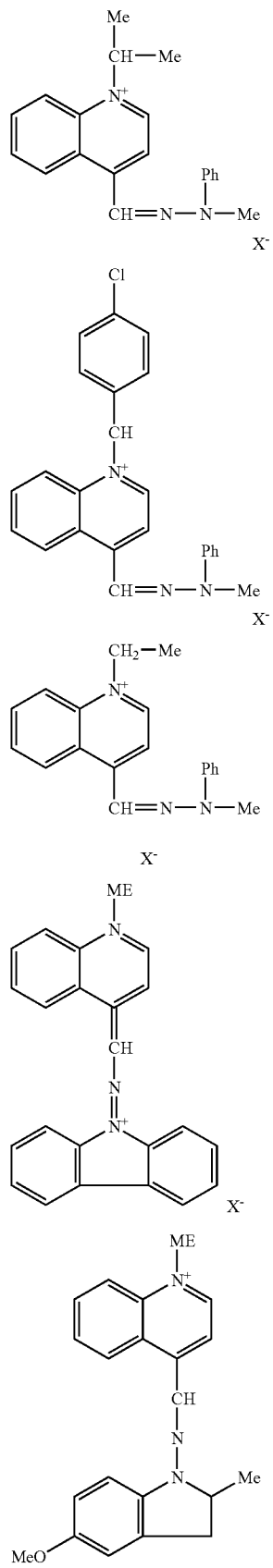
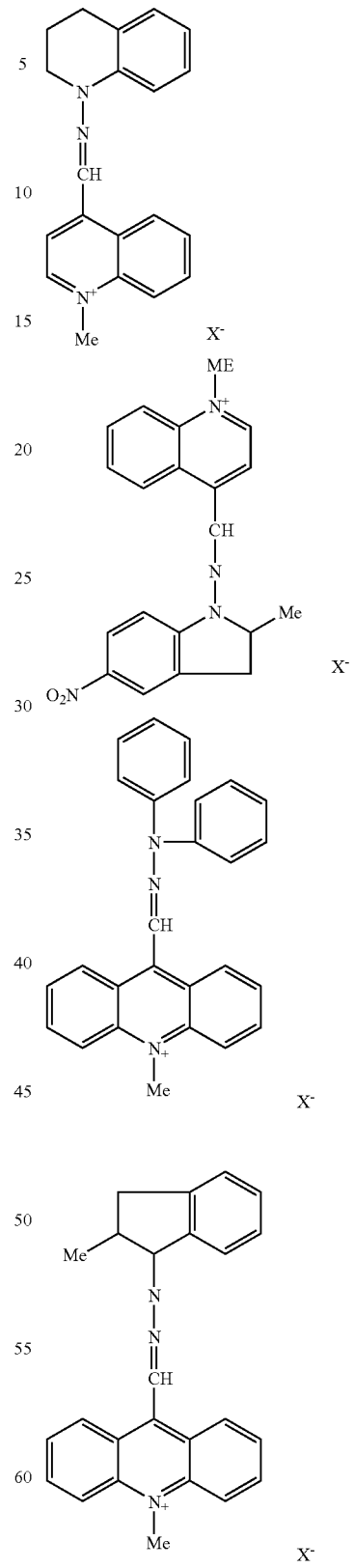
wherein X- is an anion that ensures the neutrality of the molecule.

14. The process of claim 1, wherein the at least one dye compound of formula (I) is present in an amount ranging from 0.001% to 5% by weight relative to the total weight of the dye composition.

15. The process of claim 1, wherein the composition further comprises at least one cosmetic adjuvant chosen from monoalcohols, polyols, anionic, cationic, nonionic, amphoteric and zwitterionic surfactants, mixtures thereof, and mineral or organic thickeners.

16. The process of claim 1, wherein the composition further comprises at least one thickener chosen from anionic, cationic, nonionic, and amphoteric associative polymers.

17. The process of claim 1, wherein the composition further comprises at least one oxidation base and at least one coupler.

18. A process for dyeing human keratin fibers, comprising applying to said fibers a composition comprising a dye of formula (I), optionally at least one oxidation base and optionally at least one coupler, in the presence of an oxidizing agent, wherein said dye of formula (I) is chosen from at least one direct cationic hydrazone dye of formula (I), and tautomeric forms thereof:

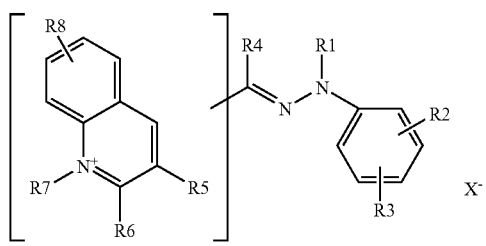

wherein
- $R_1$ and $R_7$ are, independently of each other, chosen from $C_1$-$C_6$ alkyl, $C_1$-$C_6$ hydroxyalkyl, benzyl, p-chlorobenzyl and phenyl radicals,
- $R_4$ is chosen from a hydrogen atom and $C_1$-$C_6$ alkyl radicals,
- $R_2$, $R_3$, $R_5$, $R_6$ and $R_8$ are, independently of each other, chosen from hydrogen atoms, $C_1$-$C_6$ alkyl radicals, halogen atoms, nitro radicals, $C_1$-$C_6$ alkoxy radicals, amino radicals, $C_1$-$C_6$ alkylamino radicals, $C_1$-$C_6$ dialkylamino radicals, sulfamoyl radicals, $C_1$-$C_6$ dialkylsulfamoyl radicals, $C_1$-$C_6$ dihydroxyalkylamino radicals and $C_1$-$C_6$ dihydroxyalkylamino radicals,
- $R_1$ may form, with $R_2$ or $R_3$ and the atoms to which they are attached, a saturated or unsaturated, 5-, 6- or 7-membered ring optionally substituted with at least one $C_1$-$C_6$ alkyl radical, or optionally fused with a benzene nucleus,
- $R_1$ and $R_4$ may form, together with the atoms to which they are attached, a 5-, 6- or 7-membered unsaturated ring,
- $R_5$ and $R_6$ may form, together with the atoms to which they are attached, a saturated or unsaturated 5-, 6- or 7-membered ring, wherein the bonding between the hydrazone group and the quinoline group takes place on any of the atoms of the quinoline heterocycle, and $X^-$ is an anion that ensures the neutrality of the molecule.

19. The process of claim 18, wherein the bonding between the hydrazone group and the quinoline group takes place on the quinoline heterocycle at the positions of the groups R5, R6, and/or R7.

20. A multi-compartment device for dyeing keratin fibers, wherein a first compartment contains a dye composition comprising, in a suitable medium, at least one direct cationic hydrazone dye of formula (I), or a tautomeric form thereof:

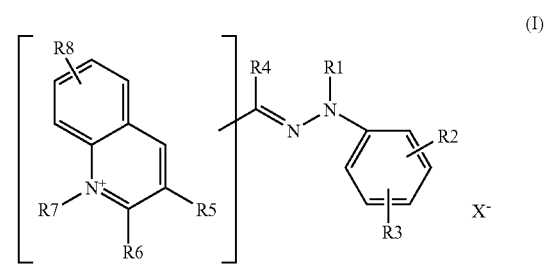

wherein
- $R_1$ and $R_7$ are, independently of each other, chosen from $C_1$-$C_6$ alkyl, $C_1$-$C_6$ hydroxyalkyl, benzyl, p-chlorobenzyl and phenyl radicals,
- $R_4$ is chosen from a hydrogen atom and $C_1$-$C_6$ alkyl radicals,
- $R_2$, $R_3$, $R_5$, $R_6$ and $R_8$ are, independently of each other, chosen from hydrogen atoms, $C_1$-$C_6$ alkyl radicals, halogen atoms, nitro radicals, $C_1$-$C_6$ alkoxy radicals, amino radicals, $C_1$-$C_6$ alkylamino radicals, $C_1$-$C_6$ dialkylamino radicals, sulfamoyl radicals, $C_1$-$C_6$ dialkylsulfamoyl radicals, $C_1$-$C_6$ dihydroxyalkylamino radicals and $C_1$-$C_6$ dihydroxyalkylamino radicals, $R_1$ may form, with $R_2$ or $R_3$ and the atoms to which they are attached, a saturated or unsaturated, 5-, 6- or 7-membered ring optionally substituted with at least one $C_1$-$C_6$ alkyl radical, or optionally fused with a benzene nucleus,
- $R_1$ and $R_4$ may form, together with the atoms to which they are attached, a 5-, 6- or 7-membered unsaturated ring,
- $R_5$ and $R_6$ may form, together with the atoms to which they are attached, a saturated or unsaturated 5-, 6- or 7-membered ring, wherein the bonding between the hydrazone group and the quinoline group takes place on any of the atoms of the quinoline heterocycle, $X^-$ is an anion that ensures the neutrality of the molecule.

and a second compartment contains an oxidizing composition.

21. The device of claim 20, wherein the bonding between the hydrazone group and the quinoline group takes place on the quinoline heterocycle at the positions of the groups R5, R6, and/or R7.

* * * * *